US012567501B2

(12) United States Patent
Ivanovska et al.

(10) Patent No.: US 12,567,501 B2
(45) Date of Patent: Mar. 3, 2026

(54) STABILITY ESTIMATION OF A POINT SET REGISTRATION

(71) Applicant: Brainlab SE, Munich (DE)

(72) Inventors: Ivana Ivanovska, Aschheim (DE); Hagen Kaiser, Icking (DE); Pablo Aponte, Haar (DE); Jochen Veigel, Rosenheim (DE)

(73) Assignee: Brainlab SE, Munich (DE)

( * ) Notice: Subject to any disclaimer, the term of this patent is extended or adjusted under 35 U.S.C. 154(b) by 127 days.

(21) Appl. No.: 17/422,352

(22) PCT Filed: Mar. 13, 2020

(86) PCT No.: PCT/EP2020/056809
§ 371 (c)(1),
(2) Date: Jul. 12, 2021

(87) PCT Pub. No.: WO2021/180333
PCT Pub. Date: Sep. 16, 2021

(65) Prior Publication Data
US 2022/0328177 A1 Oct. 13, 2022

(51) Int. Cl.
*G16H 40/63* (2018.01)
*G16H 20/40* (2018.01)

(52) U.S. Cl.
CPC .............. *G16H 40/63* (2018.01); *G16H 20/40* (2018.01)

(58) Field of Classification Search
USPC ........................................................ 705/2–3
See application file for complete search history.

(56) References Cited

U.S. PATENT DOCUMENTS 10,929,976 B2 * 2/2021 Gooding ............... G06T 11/008
2006/0142657 A1 * 6/2006 Quaid .................... A61B 90/37
600/424

(Continued)

FOREIGN PATENT DOCUMENTS

WO 2009064715 5/2009
WO 2014122301 8/2014

OTHER PUBLICATIONS

Hsu, L. (2000). Automated registration of multimodality medical images of the head using three-dimensional edges (Order No. 9951906). Available from ProQuest Dissertations and Theses Professional. (304589687). Retrieved from https://dialog.proquest.com/professional/docview/304589687?accountid=131444 (Year: 2000).*

(Continued)

*Primary Examiner* — Bennett Stephen Erickson
(74) *Attorney, Agent, or Firm* — Gray Ice Higdon

(57) ABSTRACT

The present invention relates to a method encompassing acquiring data as to the geometric structure/topology of a predefined surface section as well as to an additional physical property assigned to the surface section, determining variability of the geometric structure/topology as well as of the additional physical property over the surface section, and determining from these at variabilities an expected stability of co-registering datasets describing the predefined surface section. The present invention further relates to a corresponding computer program and a corresponding system for carrying out this method.

12 Claims, 2 Drawing Sheets

(56) References Cited

U.S. PATENT DOCUMENTS

| | | | |
|---|---|---|---|
| 2009/0093702 A1* | 4/2009 | Vollmer | G16H 40/63 |
| | | | 600/407 |
| 2016/0225144 A1* | 8/2016 | Spahn | A61B 5/7425 |
| 2017/0236294 A1 | 8/2017 | Fisher et al. | |
| 2018/0025496 A1* | 1/2018 | Lindner | G06T 17/00 |
| | | | 382/154 |
| 2018/0043182 A1* | 2/2018 | Wu | A61N 5/1039 |
| 2018/0247412 A1* | 8/2018 | Gooding | A61B 90/36 |
| 2019/0060004 A1 | 2/2019 | Witcomb et al. | |
| 2019/0130568 A1 | 5/2019 | Srimohanarajah et al. | |
| 2019/0133695 A1 | 5/2019 | Hladio et al. | |
| 2020/0289025 A1* | 9/2020 | Dichterman | G16H 40/63 |
| 2021/0196384 A1* | 7/2021 | Shelton, IV | A61B 1/0646 |
| 2022/0008131 A1* | 1/2022 | Sculco | G06T 19/006 |
| 2022/0240845 A1* | 8/2022 | Holmes | A61B 5/4833 |

OTHER PUBLICATIONS

International Search Report and Written Opinion issued for Application No. PCT/EP2020/056809 dated Nov. 26, 2020. 18 pages.
Stoddart et al. "Estimating pose uncertainty for surface registration" British Machine Vision Conference. BMVC 1996 doi:10.5244/C. 10.54. 10 pages.
Gelfand et al. "Geometrically Stable Sampling for the ICP Algorithm" Standford University. 8 pages.

* cited by examiner

STABILITY ESTIMATION OF A POINT SET REGISTRATION

FIELD OF THE INVENTION

The present invention relates to a computer-implemented method of estimating stability of co-registering point-clouds during a point set registration, a corresponding computer program, a computer-readable storage medium storing such a program and a computer executing the program, as well as a medical system comprising an electronic data storage device and the aforementioned computer.

TECHNICAL BACKGROUND

In the technical filed of computer assisted surgery and therapy, a large range of applications and appliances exist for which datasets describing three-dimensional surfaces need to be registered with each other, i.e. for which a spatial transformation has to be found, for example via an algorithm performed by a computer, that aligns these datasets. Success of such surface registrations significantly depends on the topology of the surface described by the respective datasets. The registration of featureless surfaces, such as flat or spherical surfaces regularly shows difficult, since the surfaces to be registered with each other may, for example, "slide" against each other as no correspondence can be found in the dimension parallel to the surfaces, thereby rendering the registration procedure instable.

A common approach to encounter this problem is to base the registration on additional data, which adds further topology-information to the respective surfaces. For example, data as to the color or temperature of the surface to be registered may add additional features assigned to the surface that help in finding a correspondence in an otherwise featureless dimension. However, if this additional data is also rather uniform over the surface, the registration will most probably still be instable.

The present invention has the object of estimating stability in co-registering two or more predefined datasets, for example point clouds, that describe a surface section. In other words, the approach described herein is to estimate how well the datasets describing a surface section can be registered with each other.

The present invention can be used for a wide range of procedures that involve registering datasets describing a surface section, e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring data as to the geometric structure/topology of a predefined surface section as well as to an additional physical property assigned to the surface section, determining variability of the geometric structure/topology as well as of the additional physical property over the surface section, and determining from these variabilities an expected stability of co-registering datasets describing the predefined surface section.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of estimating stability of co-registering point-clouds during a point set registration. The method comprises executing, on at least one processor of at least one computer (for example at least one computer being part of a navigation system), the following exemplary steps which are executed by the at least one processor.

In a (for example first) exemplary step, 3D-surface data is acquired which describes the spatial positions of a first plurality of points defining a surface section of a body. In other words, a dataset is acquired that describes a region of interest on which basis a point set registration procedure is planned, for example for aligning two or more datasets describing that surface with each other for registration or tracking purposes. For example, the surface section is represented by the skin surface within a predefined region of interest of a patient's body part, for example, the patient's head.

In a (for example second) exemplary step, 3D-variability data is determined based on the 3D-surface data, which describes variability of the spatial positions of the point cloud. In this subsequent step, the topology of the surface section is analyzed whether it contains any features, that for example distinguish the surface from a mere plane or sphere. For example, the amount or density of maxima and minima over the surface section as well as the amplitude(s) between these maxima and minima can indicate the geometric variability of the surface section and in turn the variability of the spatial positions of the point cloud describing that surface section.

In a (for example third) exemplary step, auxiliary data is acquired which describes a value distribution of a condition variable detected for the body surface section. In other words, that step is to acquire additional information assigned to the surface section, which may describe further features that could help in revealing a correspondence between two datasets describing this surface section.

In a (for example fourth) exemplary step, auxiliary-variability data is determined based on the auxiliary data, which describes variability of the value distribution. Quite similar to the second exemplary step described above, possible features within the value distribution are analyzed in order to estimate whether the additional information assigned to the surface section can help in finding a correspondence between two datasets describing the surface section.

In a (for example fifth) exemplary step, evaluation data is determined based on the 3D-variability data and the auxiliary-variability data, describing, for at least one translational and/or at least one rotational degree of freedom, an expected stability of co-registering the body surface section defined by the first or another plurality of points with the body surface section defined by a second plurality of points. In other words, an estimation is made with the help of the data acquired in regards to the surface section's geometric variability as well as of the variability of the additional value distribution assigned to the surface section, as to how good two or more datasets which describe the surface section can be co-registered with each other, for example by performing an Iterative-Closest-Point (ICP)-algorithm or a Normal-Distribution-Transform (NDT)-algorithm on a computer processor.

In an example of the method according to the first aspect, the values of the condition variable are assigned to the first plurality of points. While at least some of the specific values of the condition variable may generally be assigned to spatial positions on the surface section that are different to the point positions of the point cloud, each one of the points of the point cloud may be assigned to a specific value of the condition variable.

In a further example, the condition variable describes a property of the surface section in regards to
- an emission;
- a transmittance; and/or
- a reflection of electromagnetic radiation, particularly of radiation in an infrared spectrum and/or in a spectrum visible to the human eye.

For example, the condition variable may describe a distribution of one or more colors, of a grey-scale or of a temperature over the surface section. The one or more colors, the grey-scale or the temperature may be assigned to the surface section, even though the underlying electromagnetic radiation originates from another location.

In a further example, determining 3D-variability data involves establishing a 3D-score factor describing the determined variability of the spatial positions, particularly as a numeric value.

For example, the 3D-score factor may be calculated on the basis of the eigenvectors and the eigenvalues of a covariance matrix used for the error minimization of an ICP-algorithm. If, for example, the eigenvectors of this covariance matrix are $x_1$ to $x_n$, and the eigenvalues of the covariance matrix are $\lambda_1$ to $\lambda_n$, with $\lambda_n \geq \ldots \geq \lambda_n$, the 3D-score factor may be defined as $$SF_{3D} = \frac{\lambda 1}{\lambda n}.$$

If, for this specific case, one or more of the eigenvalues $\lambda_2$ to $\lambda_n$ are small as compared to $\lambda_1$, the corresponding one or more eigenvectors define a "sliding" direction in which it is likely that no correspondence can be found between the two point clouds to be registered due to a lack of characterizing features. On the other hand, if the 3D-score factor $SF_{3D}$ ranges close to 1, i.e. the eigenvalues of the covariance matrix do not spread too much, this may be an indication that an ICP-based co-registration of the two point-clouds that only considers the 3D-surface data (i.e. the geometric topology) will be stable.

In a further example, determining auxiliary-variability data involves establishing an auxiliary-score factor describing the determined variability of the value distribution, particularly as a numeric value.

In a manner similar to the approach described above in regards to the 3D-score factor, another score factor $SF_{AUX}$ can be determined for the value distribution of the condition variable. For example, the value-distribution for the temperature, one or more colors or a grey-scale over the surface section may represent sort of a "temperature/color/grey-scale topology" in a $4^{th}$ dimension on which basis a temperature, color or grey-scale score factor may be determined in the manner described above for the 3D-score factor.

In a further example, the auxiliary-score factor is established based on at least one of:
- distinctive values of the condition variable, which are assigned to a finite number of sections of the value distribution;
- a spread between the highest and the lowest value of the condition variable detected within the surface section;
- a continuous value distribution over the surface section.

Once the geometric shape and the value distribution of the condition variable has been determined over the surface section, it may be sufficient for the intended purpose when the score factor is calculated from some of that data. Thus, it may be sufficient to know about the overall spread of the point positions and/or of the values for the condition variable. For example, a small overall spread may indicate a small variability, whereas a high spread may indicate a high variability. Moreover, it may be also sufficient to know that the value distribution over the surface section contains a certain amount of prominent features, for example significant peaks and lows at some locations of the surface section.

A further example of the method described herein additionally comprises the step of determining overall-variability data, which describes an overall-variability combining the 3D-variability and the auxiliary-variability, particularly wherein an overall-score factor is established as a function of the 3D-score factor and the auxiliary-score factor, which describes the determined overall-variability, specifically as a numeric value. In other words, the variability of the geometric shape and the variability of the topology in regards to the additional condition variable can be merged, such that an overall score-factor can be calculated as a function of the 3D-score factor and of the auxiliary score-factor.

Each one of the score-factors described above may give an indication whether a co-registration of datasets describing the surface section leads to a satisfying result, with, for example, no or only negligible positional deviations between the surfaces described by the two datasets. Thus, any one of the above described score-factors, i.e. the 3D-score factor, the auxiliary-score factor and the overall-score factor may be output, for example as a numeric value and shown to a user via a graphical interface of a navigation system, such that the user can already estimate whether a co-registration of a certain and already scanned surface section is likely to lead to a satisfying result.

Further, the present invention may also relate to a model-building process for which, in a first step, anyone or all of the above-described score factors is/are related to actual outcomes of co-registrations, i.e. measured positional deviations between the two surfaces described by corresponding datasets that have been co-registered.

Thus, in a further example of the method described herein, determining evaluation data involves acquiring error data which describes, for the at least one translational and/or at least one rotational degree of freedom, an actual positional error in co-registering the body surface section defined by the first or another plurality of points and the body surface section defined by the second plurality of points via an Iterative-Closest-Point (ICP) algorithm or a Normal-Distribution-Transform (NDT)-algorithm, particularly wherein a function is determined which describes a mathematical correspondence between the positional error and the 3D-score factor and/or the auxiliary-score factor.

This approach allows to verify whether the score factors reliably "predict"—for a specific surface section—whether a planned co-registration will be performed satisfyingly.

For estimating a possible outcome of co-registering previously unknown surface sections, one or more of the above factors and the positional error data are determined for a plurality of different surface sections, wherein a model is determined which describes, over the plurality of surface sections, a mathematical correspondence between the 3D-score factor and/or the auxiliary-score factor, and the positional error.

In other words, a model is built from a sufficiently large number of co-registrations that have been performed for a plurality of different surface sections, wherein for each co-registration one or more of the above described score factors has been determined and put into relation to actual positional deviations that have been measured after the corresponding co-registrations have been performed. With a sufficiently large number of correlations between the determined score factors and the measured positional deviations, a model can be built in a known manner that allows to predict the outcome, i.e. the positional deviations to be expected when performing a co-registration procedure for a previously unknown surface section.

The model building process may also consider a ratio of a change in the temperature-distribution over time and within the surface section and/or may consider how rigid or deformable the surface section is. Both, a temperature-change and a possible deformation of the surface may be determined for a co-registration. Thus, the model may consider these factors for evaluating suitability of a surface section for co-registration.

At least one of the 3D-score factor, the auxiliary-score factor, the overall score-factor and the expected stability of co-registering the body surface section may be displayed on a graphical-user-interface (GUI), particularly in a color coded fashion and/or as a numeric value.

For example, surface sections scanned by a tracking and/or navigation system may be labelled based on the stability or an expected quality of a co-registration procedure performed on that specific surface section. Such labels may be color-coded, wherein green may indicate that a co-registration is stable and delivers a satisfying result, and red may indicate an expected unstable co-registration that likely delivers an unsatisfying result.

Further, certain appliances and applications in the medical field may comprise an automatic selection of surface sections that qualify for a stable and satisfying co-registration. For example, several possible surface section can be compared with each other by a navigation system, wherein the surface section is selected which is expected to allow the most stable co-registration and the best result.

According to a further embodiment of the method described herein, an Iterative-Closest-Point (ICP)-algorithm or a Normal-Distribution-Transform (NDT)-algorithm is performed to co-register the body surface section defined by the first plurality of points with the body surface section defined by a second plurality of points, particularly depending on whether the determined expected stability is above a predefined minimum stability threshold, specifically based on the automatic selection.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect;
b) at least one electronic data storage device storing at least the evaluation data; and
c) a medical device for carrying out a medical procedure on the patient,
    wherein the at least one computer is operably coupled to
    the at least one electronic data storage device for acquiring, from the at least one data storage device, at least the evaluation data, and
    the medical device for issuing a control signal to the medical device for controlling the operation of the medical device on the basis of the evaluation data.

Alternatively or additionally, the invention according to the fifth aspect is directed to a for example non-transitory computer-readable program storage medium storing a program for causing the computer according to the fourth aspect to execute the data processing steps of the method according to the first aspect.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registration is the process of transforming different sets of data into one co-ordinate system. The data can be multiple point clouds and/or data from different sensors, different times or different viewpoints. It is used in computer vision, medical imaging and in compiling and analysing images and data from satellites. Registration is necessary in order to be able to compare or integrate the data obtained from these different measurements.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Registering may also describe a transformation (for example, linear transformation) of an element (for example, a pixel or voxel), for example the position of an element, of a first dataset in a first coordinate system to an element (for example, a pixel or voxel), for example the position of an element, of a second dataset in a second coordinate system (which may have a basis which is different from the basis of the first coordinate system). In one embodiment, a registration is determined by comparing (for example, matching) the color values (for example grey values) of the respective elements by means of an elastic or rigid fusion algorithm. The registration is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
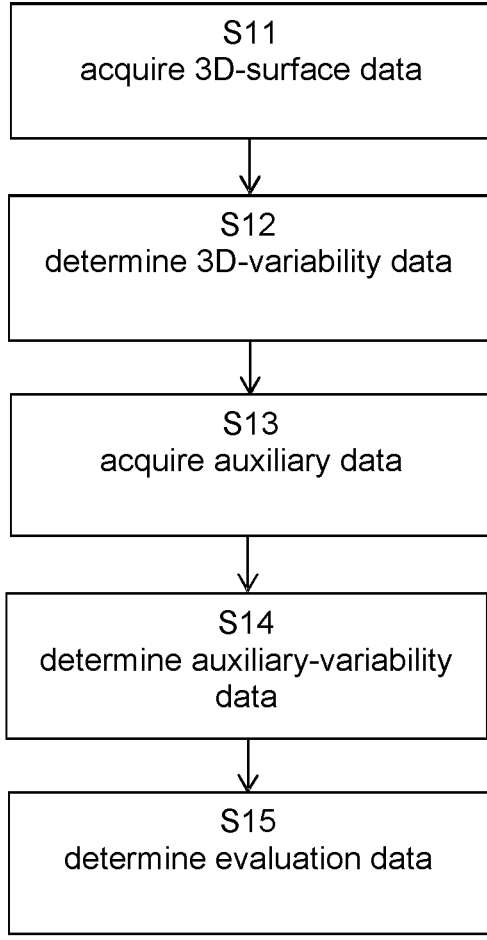
FIG. 1 shows the basic steps of the method according to the first aspect of the present invention.

FIG. 1 shows the basic steps that are performed when carrying out the method according to the present invention.

The data acquired first concerns the geometric shape of a surface section of interest in the three-dimensional space (cf. step S11) as well as the distribution of an additional physical property or condition such as the surface color or surface temperature over the surface section (cf. step S13). Both, the geometry and the additional physical property/condition can be determined via suitable sensors known in the art.

After the geometry and the additional physical property/condition of the surface section has been determined, the variability, i.e. the content of features within the surface section is calculated for the surface shape (cf. step S12) as well as for the additional surface property/condition (cf. step S14). This may include calculating numeric values that indicate the degree of variability as to the shape and/or the degree of variability as to the physical property/condition.

Since stability of a point set registration algorithm significantly depends on the degree of variability of a surface section, the numeric value(s) give an indication of how stable a co-registering procedure of this surface section can be expected to be. Thus, the numeric value(s) may be shown in conjunction with the surface section to a user/practitioner on a graphical user interface such as a display of a medical navigation system. Based on the shown numeric value(s), the user can then decide on using this particular surface section or rather another surface section with more promising numeric values, to for example base a tracking procedure requiring a surface co-registration on this particular or another surface section.

Figure 2:
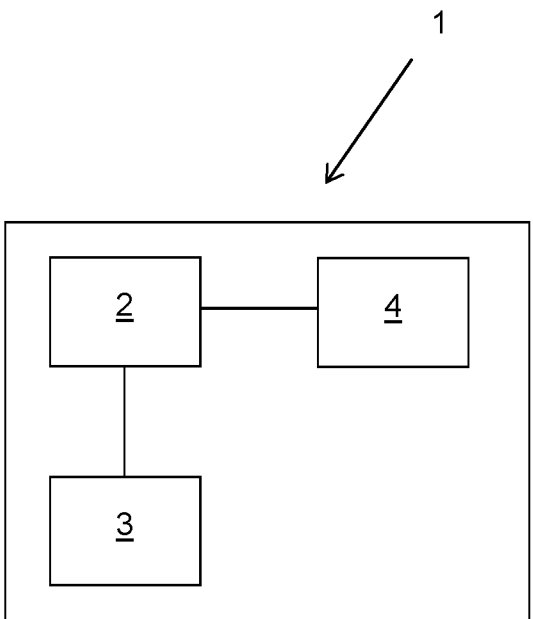
FIG. 2 shows a schematic illustration of the system according to the fifth aspect of the present invention.

FIG. 2 is a schematic illustration of the medical system 1 according to the fifth aspect. The system is in its entirety identified by reference sign 1 and comprises a computer 2, an electronic data storage device (such as a hard disc) 3 for storing at least the evaluation data and a medical device 4

(such as a medical tracking system). The components of the medical system 1 have the functionalities and properties explained above with regard to the fifth aspect of this disclosure.

The invention claimed is:

1. A computer-implemented method of estimating stability of co-registering point-clouds during a point set registration, the point-clouds defining a geometric shape of a three-dimensional surface section of a body, comprising:

acquiring, via signals received from one or more sensors, 3D-surface data which describes spatial positions of a first plurality of points defining the geometric shape of the three-dimensional surface section;

determining 3D-variability data based on the 3D-surface data, which describes variability of the spatial positions of the first plurality of points with respect to each other and across the three-dimensional surface section, wherein a 3D-score factor is established which quantifies the determined variability of the spatial positions as a single numeric value for the entire three-dimensional surface section;

acquiring, via signals received from one or more additional sensors, auxiliary data which describes a value distribution of a condition variable detected over the surface section wherein the condition variable describes a property of the surface section of at least one of:

an emission;

a transmittance; and/or a reflection of electromagnetic radiation;

determining auxiliary-variability data based on the auxiliary data, which describes variability of the value distribution of the condition variable, wherein an auxiliary-score factor is established which quantifies the determined variability of the value distribution of the condition variable over the surface section as a single numeric value for the entire three-dimensional surface section; and determining evaluation data based on the 3D-variability data and the auxiliary-variability data, involving:

determining, based at least on the 3D-score factor and the auxiliary-score factor, the evaluation data describing an expected stability of co-registering, in a three-dimensional space, the surface section as defined by a first dataset including the 3D-surface data and the auxiliary data, with the surface section as defined by a second dataset describing at least spatial positions of a second plurality of points defining the geometric shape of the surface section.

2. The method according to claim 1, wherein the auxiliary-score factor is established based on at least one of:

distinctive values of the condition variable, which are assigned to a finite number of sections of the value distribution;

a spread between the highest and the lowest value of the condition variable detected within the surface section; and a continuous value distribution over the surface section.

3. The method according to claim 1, further comprising determining overall-variability data, which describes an overall-variability combining the 3D-variability and the auxiliary-variability, wherein an overall-score factor is established as a function of the 3D-score factor and the auxiliary-score factor, which describes the determined overall-variability, specifically as a numeric value.

4. The method according to claim 3, wherein at least one of the 3D-score factor, the auxiliary-score factor, the overall score-factor and the expected stability of co-registering the surface section is displayed on a graphical-user-interface (GUI), in a colour coded fashion and/or as a numeric value.

5. The method according to claim 1, wherein the surface section is automatically selected from a plurality of possible surface sections of the body, for which a best 3D-score factor, auxiliary-score factor, overall score-factor and/or expected stability of co-registering the surface section is determined.

6. The method according to claim 1, wherein an Iterative-Closest-Point (ICP) algorithm or a Normal-Distribution-Transform (NDT) algorithm is performed to co-register the surface section defined by the first plurality of points with the surface section defined by the second plurality of points, depending on whether the determined expected stability is above a predefined minimum stability threshold.

7. The method according to claim 1, wherein determining, based at least on the 3D-score factor and the auxiliary-score factor, the evaluation data describing the expected stability of co-registering the surface section comprises:
   determining an expected positional deviation in co-registering the surface section, based on the 3D-score factor and the auxiliary-score factor and a model built from a plurality of co-registrations each performed for a respective surface section from a plurality of different surface sections,
   wherein the model describes, over the plurality of different surface sections, a mathematical correspondence between: (1) an actual positional deviation measured after performing a respective co-registration for a respective surface section, and (2) a 3D-score factor and/or an auxiliary-score factor, that are determined for the respective surface section.

8. The method according to claim 7, wherein the surface section is a previously unknown surface section in addition to the plurality of different surface sections.

9. A non-transitory computer-readable medium comprising instructions which, when executed by at least one processor of at least one computer, cause the at least one processor to:
   acquire, via signals received from one or more sensors, 3D-surface data which describes spatial positions of a first plurality of points defining a geometric shape of a three-dimensional surface section of a body;
   determine 3D-variability data based on the 3D-surface data, which describes variability of the spatial positions of the first plurality of points with respect to each other and across the three-dimensional surface section, wherein a 3D-score factor is established which quantifies describes the determined variability of the spatial positions as a single numeric value for the entire three-dimensional surface section; and
   acquire, via signals received from one or more additional sensors, auxiliary data which describes a value distribution of a condition variable detected over the surface section wherein the condition variable describes a property of the surface section of at least one of:
   an emission;
   a transmittance; and/or
   a reflection
   of electromagnetic radiation;
   determine auxiliary-variability data based on the auxiliary data, which describes variability of the value distribution of the condition variable, wherein an auxiliary-score factor is established which quantifies the determined variability of the value distribution over the surface section as a single numeric value for the entire three-dimensional surface section; and
   determine evaluation data based on the 3D-variability data and the auxiliary-variability data, involving:
      acquire error data describing, for at least one translational and/or at least one rotational degree of freedom and for each of a plurality of different surface sections that are in addition to the surface section, an actual positional deviation in co-registering, in a three-dimensional space, a respective surface section from the plurality of different surface sections,
      determine a model that describes, over the plurality of different surface sections, a mathematical correspondence between: (1) an actual positional deviation measured after performing, in the three-dimensional space, a co-registration for the respective surface section, and (2) a 3D-score factor and an auxiliary-score factor, that are determined for the respective surface section, and
      determine, utilizing the determined model and based on the 3D-score factor and the auxiliary-score factor, the evaluation data describing an expected positional deviation for co-registering, in the three-dimensional space, the surface section as defined by a first dataset including the 3D-surface data and the auxiliary data, with the surface section as defined by a second dataset describing at least spatial positions of a second plurality of points defining the geometric shape of the surface section.

10. The non-transitory computer readable medium according to claim 9, wherein the surface section is a previously unknown surface section.

11. A medical system, comprising:
   at least one computer having at least one processor; and
   having associated memory for storing instructions which cause the at least one processor to:
   acquire, via signals received from one or more sensors, 3D-surface data which describes spatial positions of a first plurality of points defining a geometric shape of a three-dimensional surface section of a body;
   determine 3D-variability data based on the 3D-surface data, which describes variability of the spatial positions of the first plurality of points with respect to each other and across the three-dimensional surface section, wherein a 3D-score factor is established which quantifies the determined variability of the spatial positions as a single numeric value for the entire three-dimensional surface section; and
   acquire, via signals received from one or more additional sensors, auxiliary data which describes a value distribution of a condition variable detected over the surface section wherein the condition variable describes a property of the surface section of at least one of:
   an emission;
   a transmittance; and/or
   a reflection
   of electromagnetic radiation;
   determine auxiliary-variability data based on the auxiliary data, which describes variability of the value distribution of the condition variable, wherein an auxiliary-score factor is established which quantifies the determined variability of the value distribution over the surface section as a single numeric value for the entire three-dimensional surface section; and
   determine evaluation data based on the 3D-variability data and the auxiliary-variability data, involving:

acquiring error data describing, for at least one translational and/or at least one rotational degree of freedom and for each of a plurality of different surface sections that are in addition to the surface section, an actual positional deviation in co-registering a respective surface section from the plurality of different surface sections, determine a model that describes, over the plurality of different surface sections, a mathematical correspondence between: (1) an actual positional deviation measured after performing a co-registration in three-dimensional space, for the respective surface section, and (2) a 3D-score factor and an auxiliary-score factor, that are determined for the respective surface section, determining, utilizing the determined model and based on the 3D-score factor and the auxiliary-score factor, the evaluation data describing an expected positional deviation for co-registering the surface section as defined by a first dataset including the 3D-surface data and the auxiliary data, with the surface section as defined by a second dataset describing at least spatial positions of a second plurality of points defining the geometric shape of the surface section;

at least one electronic data storage device storing at least the evaluation data; and a medical device for carrying out a medical procedure on a patient, wherein the at least processor is operably coupled to:

the at least one electronic data storage device for acquiring, from the at least one data storage device, at least the evaluation data, and the medical device for issuing a control signal to the medical device for controlling an operation of the medical device on the basis of the evaluation data.

12. The medical system according to claim 11, wherein the surface section is a previously unknown surface section.

* * * * *